US00PP33231P2

(12) United States Plant Patent
Olesen et al.

(10) Patent No.: US PP33,231 P2
(45) Date of Patent: Jul. 6, 2021

(54) ***CLEMATIS* PLANT NAMED 'EVIPO107'**

(50) Latin Name: *Clematis viticella*
Varietal Denomination: Evipo107

(71) Applicants: Mogens Nyegaard Olesen, Fredensborg (DK); Raymond J. Evison, Guernsey (GB)

(72) Inventors: Mogens Nyegaard Olesen, Fredensborg (DK); Raymond J. Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 16/873,991

(22) Filed: Sep. 3, 2020

(51) Int. Cl.
*A01H 6/72* (2018.01)
*A01H 5/02* (2018.01)

(52) U.S. Cl.
USPC ..... Plt./228

(58) Field of Classification Search
USPC ..... Plt./228
See application file for complete search history.

(56) References Cited

PUBLICATIONS https://www.poulsenroser.dk/en/clematis/ShowProduct/78164 2018.*

* cited by examiner

*Primary Examiner* — Annette H Para

(57) ABSTRACT

A new *Clematis* plant with a very compact growth habit, profuse, white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification:
Genus: *Clematis.*
Species: *viticella.*
Variety denomination: 'Evipo107'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo107' originated as a single seedling from the stated cross.

The new *Clematis* plant may be distinguished from its female seed parent and male pollen parent by the following characteristics. The female seed parent has a climbing habit, while the new variety has a mounding growth habit. The male seed parent has sky blue tepals while the new variety has white tepals.

The objective of the hybridization of this *Clematis* plant was to create a new and distinct variety for nursery culture with unique qualities such as:

1. Uniform and abundant white flowers;
2. Vigorous and very compact growth, making the variety suitable for container culture; and
3. Improved disease resistance.

This combination of qualities was lacking in *Clematis* plants that were in commercial cultivation and the qualities have been substantially achieved in the new variety.

'Evipo107' was selected by Mogens N. Olesen and Raymond J. Evison in their *Clematis* development program in the Channel Islands, United Kingdom in 2008. Asexual reproduction of 'Evipo107' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo107' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo107'.

Specifically illustrated in FIG. 1 of the drawings are open flowers, viewed from above and below, tepals detached revealing reproductive flower parts.

Figure 1:
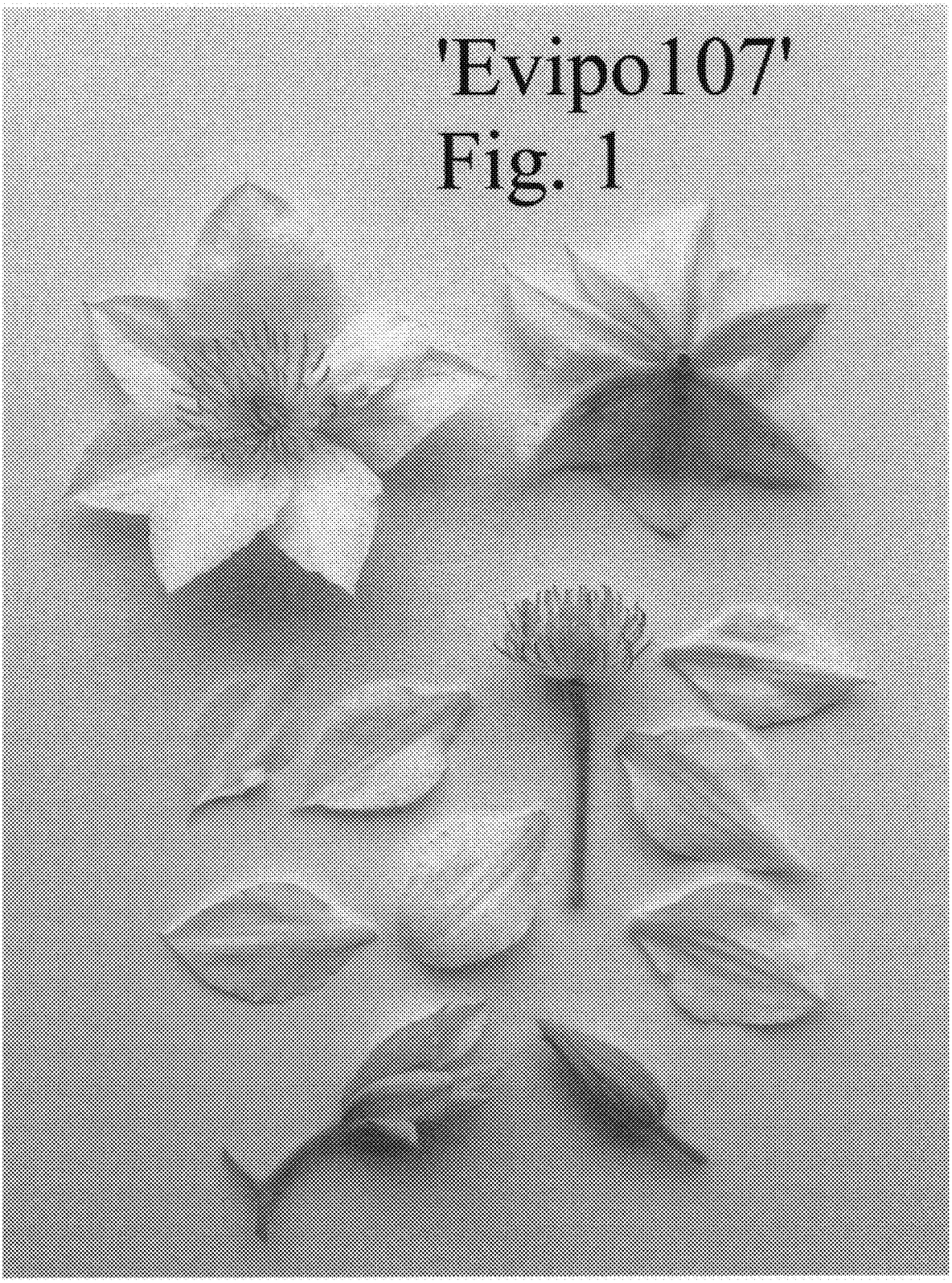
Figure 2:
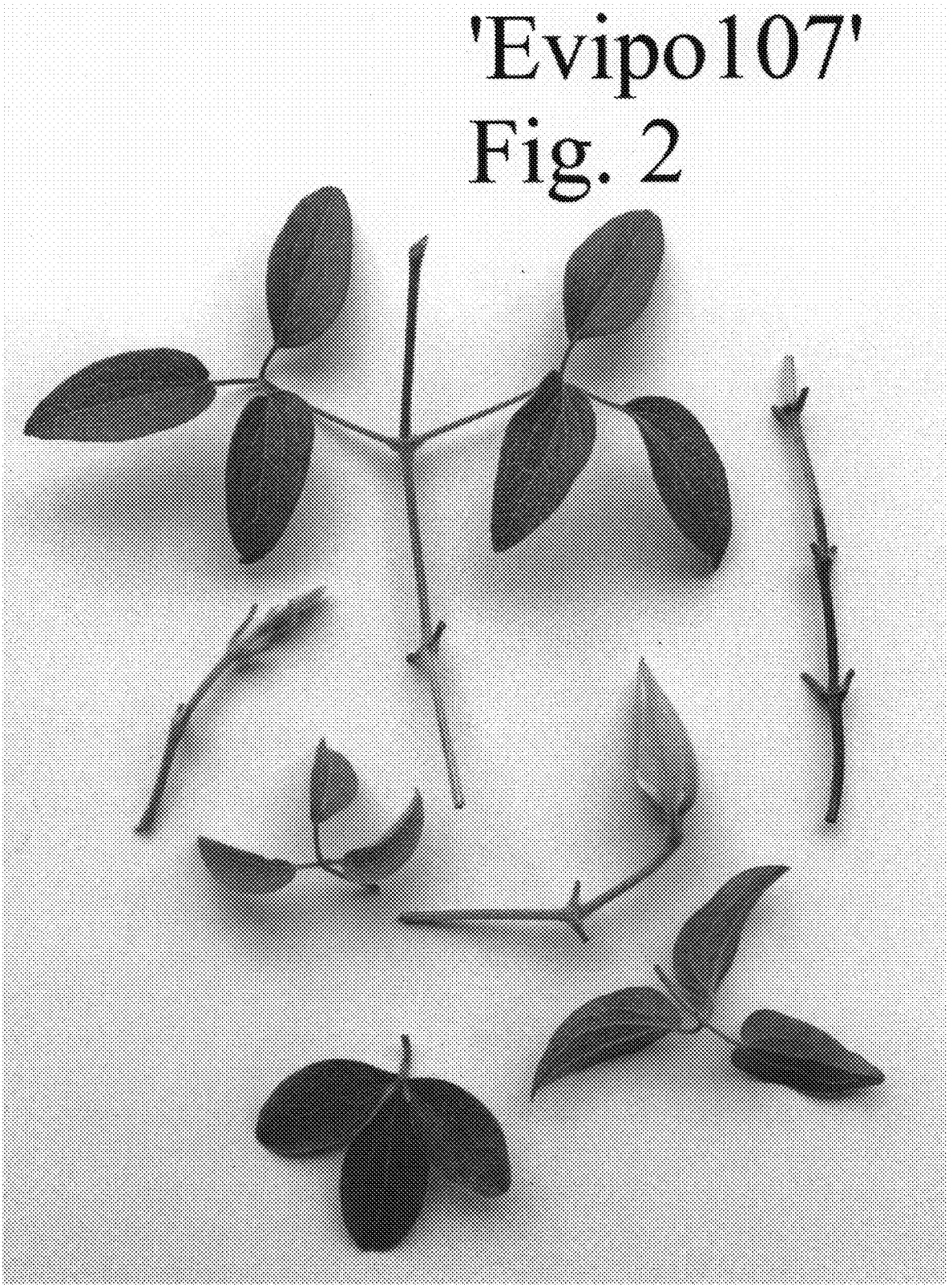

Specifically illustrated in FIG. 2 of the drawings are leaves and bare stems, and flower bud.

Figure 3:
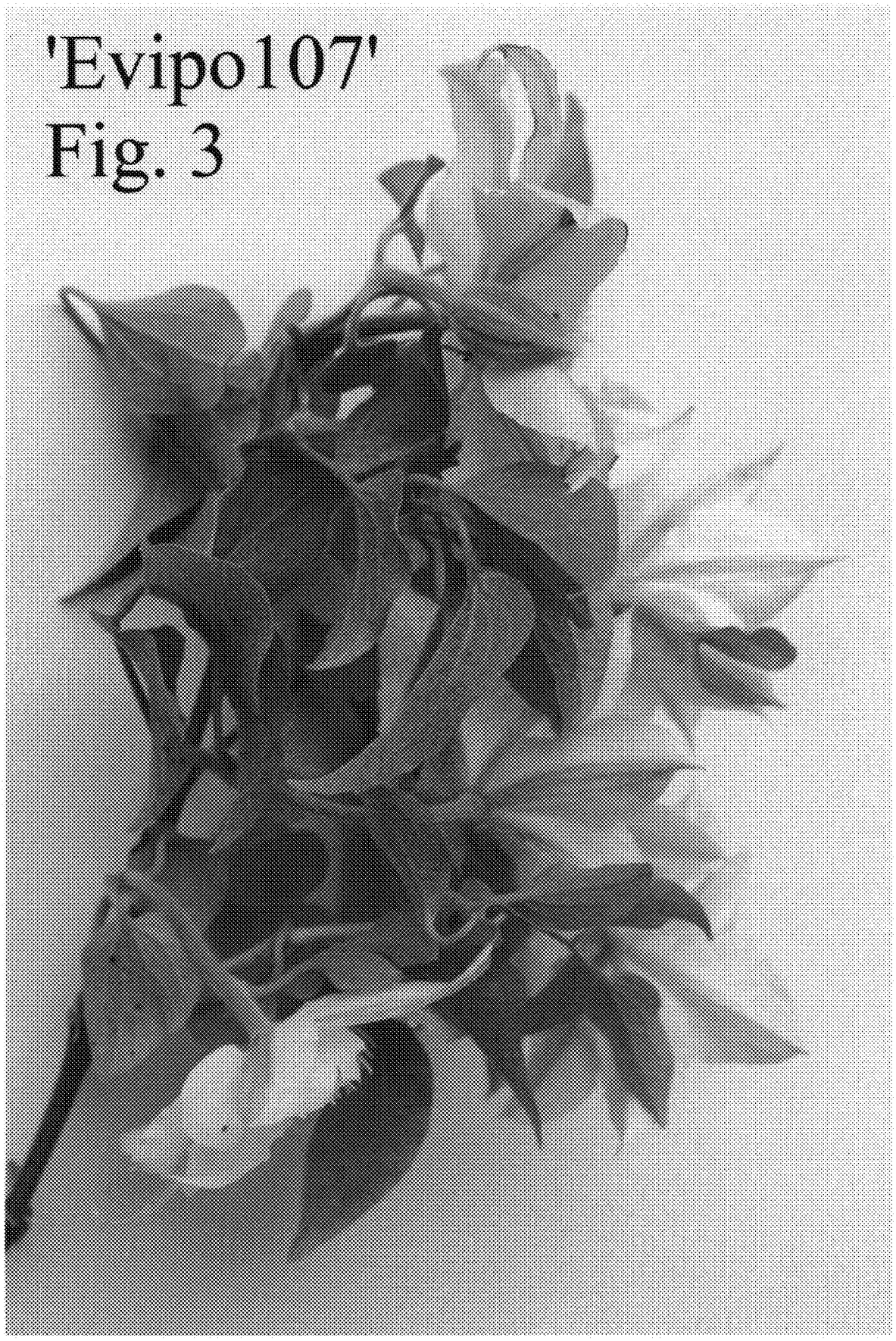

Specifically illustrated in FIG. 3 of the drawings is a cluster of flowers on the vine. Illustrated plants are 2 years of age.

DETAILED DESCRIPTION OF THE VARIETY

The following is a detailed description of 'Evipo 107', as observed in its growth throughout the flowering period in Marion County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo052' described and illustrated in U.S. Plant Pat. No. 28,600 are compared to 'Evipo107' in Chart 1.

CHART 1

| | 'Evipo107' | 'Evipo052' |
|---|---|---|
| Flower diameter | 80 mm | 120 mm |
| Tepal upper surface after opening | White Group N155D, with light intonations of Greyed-Purple Group N186D | White Group 155C |
| Tepal count | 7 | 8 |

FLOWER AND FLOWER BUD

Blooming habit: Continuous. The natural flowering period is generally from May to September.

Flower bud:
- *Size*.—About 25 mm in length and 11 mm diameter.
- *Bud form*.—Elliptic.
- *Bud color*.—Yellow-Green Group 145C.
- *Texture*.—Pubescent.

Pedicel:
- *Surface texture*.—Very pubescent.
- *Length*.—On average 25 mm in length with 2.5 mm diameter.
- *Color*.—Yellow-Green Group 145B.
- *Strength*.—Moderately strong.

Receptacle:
- *Surface texture*.—Very pubescent.
- *Shape*.—Broad funnel.
- *Size*.—1 mm (h)×3 mm (w).
- *Color*.—Yellow-Green Group 145B.

Flower arrangement:
- *Location on vine*.—New and old growth.
- *Borne*.—Along the length of the stem at the axillary buds.

Flower bloom:
- *Size*.—On average, flowers are 80 mm in diameter and 13 mm in depth.
- *Profile*.—Open flowers are flat.
- *Fragrance*.—None
- *Lasting quality*.—Flowers normally remain up to 15 days on the plant.

Tepals:
- *Tepal color*.—The upper surface is White Group N155D, with light intonations of Greyed-Purple Group N186D. The lower surface is White Group N155D with central bar Greyed-Yellow Group 160B.
- *Quantity*.—Normally 7 tepals.
- *Size*.—40 mm in length by 25 mm wide.
- *Shape*.—Individual tepal shape is elliptic. The tepal apex is acuminate. The tepal base is typically acute.
- *Apex recurvature*.—None.
- *Tepal cross section*.—Flat.
- *Margins*.—Entire. Slightly undulated.
- *Persistence*.—Tepals drop off cleanly.

Reproductive organs:
- *Pollen*.—None observed.
- *Anthers*.—Size: 5 mm in length. Color: Green-White Group 157A. Quantity: On average, 45.
- *Filaments*.—Color: White Group 155A. Length: 5 mm.
- *Pistils*.—Quantity: On average, 34.
- *Stigmas*.—Even in location relative to the length of the filaments and the height of the anthers.
- *Styles*.—Color: White Group 155A. Length: 11 mm.

Seed head characteristics: Seed not observed to date.

PLANT

Plant form: Mounding growth habit.

Plant growth: Very compact.

Size: Seasons growth attains 35 cm in height. Average spread is 35 cm.

Stems:
- *Color*.—Juvenile stems are Yellow-Green Group 145A. Mature stems are Greyed-Orange Group 176A.
- *Internodes*.—On average, 4 cm between nodes.
- *Length*.—Normally 15 cm from the base of the plant to the flowering portion of the stem.
- *Diameter*.—About 3 mm.
- *Texture*.—Mature stems are ribbed.

Plant foliage:
- *Leaf characteristics*.—Deciduous.
- *Arrangement*.—Trifoliate.
- *Leaf size*.—Compound leaves are about 95 mm (l)×95 mm (w). Leaflets are about 40 mm (l)×18 mm (w).
- *Abundance*.—On average 1 or 2 leaves per 10 cm of stem.
- *Leaf color*.—Juvenile upper Yellow-Green Group 144A. Juvenile lower Yellow-Green Group 145B. Mature upper Yellow-Green Group 144A. Mature lower Yellow-Green Group 144B.
- *Stipules*.—Absent.
- *Petioles*.—Size: Normally 30 mm in length by 1.5 mm diameter. Texture: Smooth. Color: Yellow-Green Group N144B.
- *Petioloule*.—Size: About 12 mm in length by 1.5 mm diameter. Texture: Smooth. Color: Yellow-Green Group N144B.
- *Leaflet shape*.—Elliptic. The base is acute, apex acute.
- *Margin*.—Entire.
- *Surface*.—The upper side is smooth, the lower side is rugose.
- *Thickness*.—Moderate.
- *Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo107', substantially as described and illustrated , due to its abundant white flowers with good keepabilily, attractive long lasting foliage and very compact growth, year round flowering under glasshouse conditions, suitability for production from softwood cuttings in pots, durable flowers and foliage which make the variety suitable for distribution in the floral industry.

* * * * *

'Evipo107'

'Evipo107'